US008618136B2

(12) United States Patent
Zeldis

(10) Patent No.: US 8,618,136 B2
(45) Date of Patent: *Dec. 31, 2013

(54) METHODS FOR THE TREATMENT OF MYELOPROLIFERATIVE DISEASES USING 4-(AMINO)-2-(2,6-DIOXO(3-PIPERIDYL))-ISOINDOLINE-1,3-DIONE

(75) Inventor: Jerome B. Zeldis, Princeton, NJ (US)

(73) Assignee: Celgene Corporation, Summit, NJ (US)

( * ) Notice: Subject to any disclaimer, the term of this patent is extended or adjusted under 35 U.S.C. 154(b) by 1054 days.

This patent is subject to a terminal disclaimer.

(21) Appl. No.: 11/371,777

(22) Filed: Mar. 8, 2006

(65) Prior Publication Data

US 2006/0166932 A1   Jul. 27, 2006

Related U.S. Application Data

(62) Division of application No. 10/411,656, filed on Apr. 11, 2003, now Pat. No. 7,563,810.

(60) Provisional application No. 60/424,730, filed on Nov. 6, 2002.

(51) Int. Cl.
*A61K 31/445* (2006.01)
*A61K 31/435* (2006.01)

(52) U.S. Cl.
USPC ........................... 514/323; 514/319; 514/277

(58) Field of Classification Search
USPC ......................................... 514/323, 319, 277
See application file for complete search history.

(56) References Cited

U.S. PATENT DOCUMENTS

| | | | |
|---|---|---|---|
| 4,604,463 A | 8/1986 | Miyasaka et al. |
| 4,847,276 A | 7/1989 | Yarrington |
| 4,894,456 A | 1/1990 | Wall et al. |
| 4,939,255 A | 7/1990 | Tagawa et al. |
| 4,943,579 A | 7/1990 | Vishnuvajjala et al. |
| 4,981,968 A | 1/1991 | Wall et al. |
| 5,004,758 A | 4/1991 | Boehm et al. |
| 5,049,668 A | 9/1991 | Wall et al. |
| 5,053,512 A | 10/1991 | Wani et al. |
| 5,061,800 A | 10/1991 | Yaegashi et al. |
| 5,106,742 A | 4/1992 | Wall et al. |
| 5,122,526 A | 6/1992 | Wall et al. |
| 5,122,606 A | 6/1992 | Wani et al. |
| 5,180,722 A | 1/1993 | Wall et al. |
| 5,225,404 A | 7/1993 | Giovannella et al. |
| 5,227,380 A | 7/1993 | Wall et al. |
| 5,244,903 A | 9/1993 | Wall et al. |
| 5,340,817 A | 8/1994 | Wall et al. |
| 5,364,858 A | 11/1994 | Wall et al. |
| 5,385,901 A | 1/1995 | Kaplan et al. |
| 5,391,745 A | 2/1995 | Danishefsky et al. |
| 5,401,747 A | 3/1995 | Wall et al. |
| 5,430,057 A | 7/1995 | Andersson et al. |
| 5,446,047 A | 8/1995 | Danishefsky et al. |
| 5,447,936 A | 9/1995 | Hausheer et al. |
| 5,468,754 A | 11/1995 | Hausheer et al. |
| 5,525,731 A | 6/1996 | Danishefsky et al. |
| 5,541,327 A | 7/1996 | Danishefsky et al. |
| 5,552,154 A | 9/1996 | Giovanella et al. |
| 5,587,459 A | 12/1996 | Uckun |
| 5,593,990 A | 1/1997 | D'Amato |
| 5,597,829 A | 1/1997 | Hausheer et al. |
| 5,604,233 A | 2/1997 | Hausheer et al. |
| 5,618,709 A | 4/1997 | Gewirtz et al. |
| 5,629,327 A | 5/1997 | D'Amato |
| 5,633,260 A | 5/1997 | Hausheer et al. |
| 5,635,517 A * | 6/1997 | Muller et al. ................. 514/323 |
| 5,643,915 A | 7/1997 | Andrulis, Jr. et al. |
| 5,646,159 A | 7/1997 | Wall et al. |
| 5,648,239 A | 7/1997 | Hawkins et al. |
| 5,658,920 A | 8/1997 | Terasawa et al. |
| 5,674,874 A | 10/1997 | Hausheer et al. |
| 5,698,579 A | 12/1997 | Muller |
| 5,712,291 A | 1/1998 | D'Amato |
| 5,728,868 A | 3/1998 | Springer et al. |
| 5,734,033 A | 3/1998 | Reed |
| 5,798,368 A | 8/1998 | Muller et al. |
| 5,801,167 A | 9/1998 | Bedeschi et al. |
| 5,840,745 A | 11/1998 | Buzzetti et al. |
| 5,863,904 A | 1/1999 | Nabel et al. |
| 5,866,332 A | 2/1999 | Cocks et al. |
| 5,872,223 A | 2/1999 | Uckun |

(Continued)

FOREIGN PATENT DOCUMENTS

| WO | WO 98/03502 | 1/1998 |
|---|---|---|
| WO | WO98/46642 | 10/1998 |

(Continued)

OTHER PUBLICATIONS

Merck Manual of Diagnosis and Therapy, Myeloproliferative Disorders, 1999, Merck Research Laboratories, 17th Ed., 895-902.*
http://www.merck.com/mmpe/print/sec11/ch141/ch141a.html, Introduction:Myeloproliferative Disorders:Merck Manual Professional, 2005—printed Feb. 25, 2008, 2 pages.*
http://www.merck.com/mmpe/print/sec11/ch141/ch14ca.html, Myelofibrosis:myeloproliferative Disorders:Merck Manual Professional, Nov. 2005—printed Feb. 25, 2008, 2 pages.*
http://www.merck.com/mmpe/print/sec11/ch141/ch14ba.html, Essential Thrombocythemia:Myeloproliferative Disorders:Merck Manual Professional, 2005—printed Feb. 25, 2008, 3 pages.*
Vippagunta et al., Crystalline solids, 2001, Advanced:Drug Delivery Reviews, 48, 3-26.*

(Continued)

*Primary Examiner* — Gigi Huang
(74) *Attorney, Agent, or Firm* — Jones Day

(57) ABSTRACT

Methods of treating, preventing and/or managing a myeloproliferative disease are disclosed. Specific methods encompass the administration of an immunomodulatory compound, or a pharmaceutically acceptable salt, solvate, hydrate, stereoisomer, clathrate, or prodrug thereof, alone or in combination with a second active agent, and/or the transplantation of blood or cells. Particular second active agents are capable of suppressing the overproduction of hematopoietic stem cells or ameliorating one or more of the symptoms of a myeloproliferative disease. Pharmaceutical compositions, single unit dosage forms, and kits suitable for use in methods of the invention are also disclosed.

26 Claims, No Drawings

(56) References Cited

U.S. PATENT DOCUMENTS

| | | |
|---|---|---|
| 5,874,448 A | 2/1999 | Muller et al. |
| 5,877,200 A | 3/1999 | Muller |
| 5,885,834 A | 3/1999 | Epstein |
| 5,889,017 A | 3/1999 | Giovanella et al. |
| 5,911,995 A | 6/1999 | Uckun |
| 5,916,896 A | 6/1999 | Wall et al. |
| 5,922,844 A | 7/1999 | Hawkins et al. |
| 5,925,376 A | 7/1999 | Heng |
| 5,929,117 A | 7/1999 | Muller et al. |
| 5,932,588 A | 8/1999 | Wall et al. |
| 5,955,476 A | 9/1999 | Muller et al. |
| 5,958,769 A | 9/1999 | Roberts et al. |
| 5,985,877 A | 11/1999 | Dionne et al. |
| 5,998,596 A | 12/1999 | Bergan et al. |
| 6,034,053 A | 3/2000 | Uckun et al. |
| 6,040,305 A | 3/2000 | Taveras et al. |
| 6,040,313 A | 3/2000 | Wall et al. |
| 6,043,367 A | 3/2000 | Roffler et al. |
| 6,051,574 A | 4/2000 | Anthony |
| 6,051,582 A | 4/2000 | Taveras |
| 6,054,466 A | 4/2000 | Ciccarone et al. |
| 6,057,300 A | 5/2000 | Nabel et al. |
| 6,063,814 A | 5/2000 | Chang et al. |
| 6,063,930 A | 5/2000 | Dinsmore et al. |
| 6,066,738 A | 5/2000 | Dinsmore et al. |
| 6,071,935 A | 6/2000 | Lyssikatos |
| 6,071,948 A | 6/2000 | D'Amato |
| 6,075,015 A | 6/2000 | Sestelo et al. |
| 6,077,853 A | 6/2000 | Graham et al. |
| 6,080,870 A | 6/2000 | Anthony et al. |
| 6,090,948 A | 7/2000 | Dinsmore et al. |
| 6,093,737 A | 7/2000 | Anthony et al. |
| 6,096,300 A | 8/2000 | Hromas |
| 6,103,723 A | 8/2000 | Bergman et al. |
| 6,107,457 A | 8/2000 | Arlinghaus et al. |
| 6,107,520 A | 8/2000 | Rinehart et al. |
| 6,121,320 A | 9/2000 | Doukas |
| 6,124,295 A | 9/2000 | Taveras et al. |
| 6,124,465 A | 9/2000 | Bourzat et al. |
| 6,127,366 A | 10/2000 | Kim et al. |
| 6,127,406 A | 10/2000 | Gunasekera et al. |
| 6,133,303 A | 10/2000 | Bikker et al. |
| 6,143,738 A | 11/2000 | Zasloff |
| 6,143,766 A | 11/2000 | Kaltenbronn et al. |
| 6,156,733 A | 12/2000 | Ferrara et al. |
| 6,159,984 A | 12/2000 | Guzi et al. |
| 6,169,096 B1 | 1/2001 | Venet et al. |
| 6,172,112 B1 | 1/2001 | Brouillette et al. |
| 6,183,744 B1 | 2/2001 | Goldenberg |
| 6,183,988 B1 | 2/2001 | Bloch et al. |
| 6,187,287 B1 | 2/2001 | Leung et al. |
| 6,187,786 B1 | 2/2001 | Venet et al. |
| 6,204,364 B1 | 3/2001 | Todaro et al. |
| 6,211,193 B1 | 4/2001 | Remiszewski et al. |
| 6,218,372 B1 | 4/2001 | Nabel et al. |
| 6,218,406 B1 | 4/2001 | Bourzat et al. |
| 6,218,410 B1 | 4/2001 | Uehata et al. |
| 6,218,412 B1 | 4/2001 | Thorwart et al. |
| 6,221,873 B1 | 4/2001 | Havlicek et al. |
| 6,225,322 B1 | 5/2001 | Cooper et al. |
| 6,225,323 B1 | 5/2001 | Yatscoff et al. |
| 6,225,325 B1 | 5/2001 | Jacob |
| 6,228,856 B1 | 5/2001 | Njoroge et al. |
| 6,228,865 B1 | 5/2001 | Doll et al. |
| 6,228,879 B1 | 5/2001 | Green et al. |
| 6,231,893 B1 | 5/2001 | Singhal |
| 6,232,338 B1 | 5/2001 | Davies et al. |
| 6,239,140 B1 | 5/2001 | Cooper et al. |
| 6,242,196 B1 | 6/2001 | Spiegelman et al. |
| 6,245,759 B1 | 6/2001 | Bilodeau et al. |
| 6,248,756 B1 | 6/2001 | Anthony et al. |
| 6,251,882 B1 | 6/2001 | Uckun et al. |
| 6,258,779 B1 | 7/2001 | Tsai et al. |
| 6,262,053 B1 | 7/2001 | Uckun et al. |
| 6,265,422 B1 | 7/2001 | Bikker et al. |
| 6,265,427 B1 | 7/2001 | Camden |
| 6,268,363 B1 | 7/2001 | Lee et al. |
| 6,271,242 B1 | 8/2001 | Barbacid |
| 6,277,832 B1 | 8/2001 | Sugiyama et al. |
| 6,281,230 B1 | 8/2001 | Muller et al. |
| 6,300,501 B1 | 10/2001 | Dorbrusin et al. |
| 6,303,646 B1 | 10/2001 | Lu et al. |
| 6,306,393 B1 | 10/2001 | Goldenberg |
| 6,313,129 B1 | 11/2001 | Uckun et al. |
| 6,316,471 B1 | 11/2001 | Muller et al. |
| 6,326,205 B1 | 12/2001 | Murray et al. |
| 6,326,378 B1 | 12/2001 | Friebe et al. |
| 6,329,497 B1 | 12/2001 | Boger |
| 6,331,642 B1 | 12/2001 | Batcho et al. |
| 6,333,309 B1 | 12/2001 | Higashio et al. |
| 6,335,156 B1 | 1/2002 | Hermeking et al. |
| 6,335,349 B1 | 1/2002 | Muller et al. |
| 6,342,487 B1 | 1/2002 | Riou et al. |
| 6,342,765 B1 | 1/2002 | Arnould |
| 6,346,246 B1 | 2/2002 | Kirkness et al. |
| 6,362,188 B1 | 3/2002 | Guzi et al. |
| 6,369,034 B1 | 4/2002 | Doherty et al. |
| 6,372,747 B1 | 4/2002 | Taveras et al. |
| 6,380,239 B1 | 4/2002 | Muller et al. |
| 6,383,790 B1 | 5/2002 | Shokat |
| 6,387,905 B2 | 5/2002 | Njoroge et al. |
| 6,395,754 B1 | 5/2002 | Muller et al. |
| 6,395,771 B1 | 5/2002 | Ramadoss et al. |
| 6,399,615 B1 | 6/2002 | Guzi et al. |
| 6,399,633 B1 | 6/2002 | Dumont et al. |
| 6,399,664 B2 | 6/2002 | Smith |
| 6,403,581 B1 | 6/2002 | Ayral-Kaloustian et al. |
| 6,403,613 B1 | 6/2002 | Man et al. |
| 6,410,539 B1 | 6/2002 | Arnould |
| 6,410,541 B2 | 6/2002 | Remiszewski et al. |
| 6,414,145 B1 | 7/2002 | Boyle et al. |
| 6,420,378 B1 | 7/2002 | Rubinfeld |
| 6,420,387 B1 | 7/2002 | Venet et al. |
| 6,420,391 B1 | 7/2002 | Konishi et al. |
| 6,420,414 B1 | 7/2002 | D'Amato |
| 6,432,925 B1 | 8/2002 | Hoon et al. |
| 6,432,959 B1 | 8/2002 | Cooper et al. |
| 6,436,960 B1 | 8/2002 | Shin et al. |
| 6,440,974 B2 | 8/2002 | Doll et al. |
| 6,451,812 B1 | 9/2002 | End et al. |
| 6,458,349 B1 | 10/2002 | Li et al. |
| 6,458,810 B1 | 10/2002 | Muller et al. |
| 6,458,935 B1 | 10/2002 | Burns et al. |
| 6,469,045 B1 | 10/2002 | D'Amato |
| 6,476,052 B1 | 11/2002 | Muller et al. |
| 6,518,265 B1* | 2/2003 | Kato et al. ................. 514/228.5 |
| 6,518,298 B2 | 2/2003 | Green et al. |
| 6,555,554 B2 | 4/2003 | Muller et al. |
| 6,673,828 B1 | 1/2004 | Green et al. |
| 2001/0021380 A1 | 9/2001 | Pluenneke |
| 2001/0056114 A1 | 12/2001 | D'Amato |
| 2002/0052398 A1 | 5/2002 | D'Amato |
| 2002/0054899 A1 | 5/2002 | Zeldis |
| 2002/0061923 A1 | 5/2002 | D'Amato |
| 2002/0161023 A1 | 10/2002 | D'Amato |
| 2002/0173658 A1 | 11/2002 | Muller et al. |
| 2002/0183360 A1 | 12/2002 | Muller et al. |
| 2003/0028028 A1 | 2/2003 | Man et al. |
| 2003/0045552 A1 | 3/2003 | Robarge et al. |
| 2003/0069428 A1 | 4/2003 | Muller et al. |
| 2003/0096841 A1 | 5/2003 | Robarge et al. |
| 2003/0139451 A1 | 7/2003 | Shah et al. |
| 2003/0144325 A1 | 7/2003 | Muller et al. |
| 2003/0181428 A1 | 9/2003 | Green et al. |
| 2003/0187024 A1 | 10/2003 | D'Amato |
| 2003/0191098 A1 | 10/2003 | D'Amato |
| 2003/0235909 A1 | 12/2003 | Hariri et al. |
| 2004/0028660 A1 | 2/2004 | Hariri et al. |
| 2004/0029832 A1 | 2/2004 | Zeldis |
| 2004/0077685 A1 | 4/2004 | Figg et al. |
| 2004/0077686 A1 | 4/2004 | Dannenberg et al. |
| 2004/0087546 A1 | 5/2004 | Zeldis |
| 2004/0091455 A1 | 5/2004 | Zeldis |
| 2004/0122052 A1 | 6/2004 | Muller et al. |

(56) References Cited

U.S. PATENT DOCUMENTS

FOREIGN PATENT DOCUMENTS

| WO | WO 98/54170 | | 12/1998 |
|---|---|---|---|
| WO | WO 00/09506 | * | 2/2000 |
| WO | WO 01/43743 A1 | | 6/2001 |
| WO | WO 01/87306 | | 11/2001 |
| WO | WO 01/87307 | | 11/2001 |
| WO | WO 02/42303 | | 5/2002 |
| WO | WO 02/059106 | | 8/2002 |
| WO | WO 02/064083 | | 8/2002 |
| WO | WO 2004/035064 | | 4/2004 |
| WO | WO 2004/037199 A2 | | 5/2004 |

OTHER PUBLICATIONS

Zips et al., New Anticancer Agents: Invitro and In Vivo Evaluation, 2005, in vivo, 19, 1-8.*
www.mayoclinic.com, Myelofibrosis with Myeloid Metaplasia, 2009, http://www.mayoclinic.org/myelofibrosis/ printed Aug. 19, 2009, 1 page.*
Cecil Textbook of Medicine, Agnogenic Myeloid Metaplasia, editied by Bennett et al., W.B. Saunders Company, 1996, 20th Edition, 924-925, 6 pages.*
U.S. Appl. No. 10/732,867, Dec. 9, 2003, D'Amato et al.
U.S. Appl. No. 09/545,654, Apr. 10, 2000, D'Amato.
U.S. Appl. No. 09/287,377, Apr. 7, 1999, D'Amato.
Bennett and Plum, eds., 1996, *Cecil Textbook of Medicine*, 20$^{th}$ edition, W.B. Saunders Company, pp. 920-926, 502-503.
Braunwald et al., eds., 2001, *Harrison's Principles of Internal Medicine*, 15$^{th}$ edition, McGraw-Hill, pp. 701-703.
Caponigro, 2002, "Farnesyl transferase inhibitors: a major breakthrough in anticancer therapy?" *Anticancer Drugs* (8):891-897.
Corral et al., 1999, *Ann. Rheum. Dis.* 58(Supp. 1):1107-1113.
Costa et al., 1998, *Blood* 92(10 Suppl. 1):235b.
Daley et al., 1990, "Induction of chronic myelogenous leukemia in mice by the P210bcr/abl gene of the Philadelphia chromosome," *Science* 247(4944):824-830.
D'Amato et al., 1994, "Thalidomide is an inhibitor of angiogenesis," *PNAS USA* 91:4082-4085.
Ehrenpreis et al., 1999, "Thalidomide therapy for patients with refractory Crohn's disease: an open-label trial," *Gastroenterology* 117(6):1271-1277.
Kantarjian et al., 2002, "Treatment of philadelphia chromosome-positive, accelerated-phase chronic myelogenous leukemia with imatinib mesylate," *Clin. Cancer Res.* 8(7):2167-2176.
Koch, 1985, "Thalidomide and congeners as anti-inflammatory agents," *Prog. Med. Chem.* 22:165-242.
Kropff, 2000, *Blood* 96(11 part 1):168a.
Kurzrock et al., 1988, "The molecular genetics of Philadelphia chromosome-positive leukemias," *N. Engl. J. Med.* 319(15):990-998.
Martyr, 1991, *Leuk. Lymphoma* 6:1.
Marx et al., 1999, *Proc. Am. Soc. Clin.Oncol.* 18:454a.
McCann, 1999, *Drug Topics* 41-42.
Moller et al., 1997, "Inhibition of IL-12 production by thalidomide," *J. Immunol.* 159(10):5157-5161.
Moreau et al., 1998, "Syntheses and biological evaluation of indolocarbazoles, analogues of rebeccamycin, modified at the imide heterocycle," *J. Med. Chem.* 41(10):1631-1640.
Muller et al., 1999, "Amino-substituted thalidomide analogs: potent inhibitors of TNF-alpha production," *Bioorg. Med Chem. Lett.* 9(11):1625-1630.
Muller et al., 1998, "Thalidomide analogs and PDE4 inhibition," *Bioorg. Med. Chem. Lett.* 8(19):2669-2674.
Muller et al., 1996, "Structural modifications of thalidomide produce analogs with enhanced tumor necrosis factor inhibitory activity," *J. Med. Chem.* 39(17):3238-3240.
Munshi et al., 1999, *Blood* 94(10 part 1):578a.
Penichet et al., 2001, "Antibody-cytokine fusion proteins for the therapy of cancer," *J. Immunol. Methods* 248(1-2):91-101.
*Physician's Desk Reference*, 2002, 56th edition, pp. 1154-1158; 1755-1760.

Rothenberg, 1997, "Topoisomerase I inhibitors: review and update," *Ann. Oncol.* 8(9):837-855.
Singhal et al., 1999, "Antitumor activity of thalidomide in refractory multiple myeloma," *N. Engl. J. Med.* 341(21):1565-1571.
Tefferi et al., 1994, "Issues in the diagnosis and management of essential thrombocythemia," *Mayo Clin. Proc.* 69(7):651-655.
Tierney et al., eds., 1998, *Current Medical Diagnosis and Treatment*, 37$^{th}$ edition, Appleton & Lange, pp. 499-502.
Vasiliauskas et al., 1999, "An open-label pilot study of low-dose thalidomide in chronically active, steroid-dependent Crohn's disease," *Gastroenterology* 117(6):1278-1287.
Wolff, ed., 1995, *Burger's Medicinal Chemistry and Drug Discovery*, 5$^{th}$ edition, pp. 172-178, 949-982.
U.S. Appl. No. 10/732,867, D'Amato et al.
U.S. Appl. No. 09/545,654, D'Amato.
U.S. Appl. No. 09/287,377, D'Amato.
Manrtyr, 1991, *Leuk. Lymphoma* 6:1.
Moller et al., 1997, "Inhibition of IL-12 production by thalidomide," *J. Immunol.* 159(10):5157-5161.
Muller et al., 1999, "Amino-substituted thalidomide analogs: potent inhibitors of TNF-alpha production," *Bioorg. Med. Chem. Lett.* 9(11):1625-1630.
Strasser et al., "Thalidomide treatment in multiple myeloma," Science Direct-Blood review, Sep. 20, 2002.
Muller et al., "Amino substituted thalidomide analogs: potent inhibitors . . . ," Bioorganic & Medical Chemistry Letters, vol. 9 (1999).
Raza et al., "Thalidomide produces transfusion independence in . . . ," Blood, Aug. 15, 2001, vol. 98, No. 4, pp. 958-965.
Ayalew Tefferi et al., "Lenalidomide therapy in myelofibrosis with myeloid metaplasia," Blood, Aug. 2006, 108(4):1158-1164.
Tefferi et al., Abstract # 663, Pomalidomide Therapy in Anemic Patients with Myelofibrosis: Results from a Phase-2 Randomized Multicenter Study, American Society of Hematology, 50th Annual Meeting and Exposition, Dec. 6-9, 2008, San Francisco, CA.
Kastritis, The evolving role of lenalidomide in the treatment of hematologic malignancies, Expert Opin. Pharmacother. (2007) 8(4): 497-509.
Notice of Reasons for Rejection for Japanese Patent Application No. 2004-551395.
Office Action of Canadian Patent Application No. 2,504,663.
Silver, R. T., Interferon-α2b: A New Treatment for Polycythemia Vera, Ann Intern Med, 1993, vol. 119, No. 11, p. 1091-2.
Thomas, D. A., Seminars in Hematology, vol. 37 (1), Suppl. 3, pp. 26-34 (2000).
Barosi et al., British J. Hematology, vol. 114, pp. 78-83 (2001).
Dredge et al., J. Immunology, vol. 168 (10), pp. 4914-4919 (May 2002).
Richardson et al., Blood, vol. 100 (9), pp. 3063-3067.
Tefferi, A., et al., "Pomalidomide is Active in the Treatment of Anemia Associated with Myelofibrosis," *Journal of Clinical Oncology*, 2009, 27(27):1-7.
Albitar, M., "Myeloproliferative Diseases: Molecular Genetics," *Encyclopedia of Life Sciences*, 2005, 1-6.
Beers, MH. et al., "141 Myeloproliferative Disorders," The Merck Manual of Diagnosis and Therapy, 18$^{th}$ Ed., 2006, 1098-1011.
Mesa, R., "The Therapy of Myelofibrosis: Targeting Pathogenesis," *International Journal of Hematology*, 2002, 76(suppl. 2):296-304.
Elliott, M., et al., "Thalidomide treatment in myelofibrosis with myeloid metaplasia," *British Journal of Haematology*, 2002, 117, 288-296.
English translation of Office Action dated Nov. 17, 2009 in JP Patent Application No. 2004-551395.
Office Action dated Nov. 4, 2008 in EP Patent Application No. 03731018.2.
Onida, F. and Reran, M., "Chronic myelomonocytic leukemia: myeloproliferative variant." *Curr. Hematol. Rep.*, 2004, 3(3):218-26.
European Search Report in correspondina, EP Application No. 10162202.5 dated Feb. 28, 2012.
Notice of Rejection in corresponding JP Application No. 2010-265012 dated Jan. 18, 2013 (with English summary).
Dredge, K. et al., "Novel thalidomide analogues display anti-angiogenic activity independently of immunomodulatory effects," *British Journal of Cancer*, 2002, 87:1166-1172.

(56) References Cited

OTHER PUBLICATIONS

Tsimberidou, A-M and Giles, F., "TNF-α targeted therapeutic approaches in patients with hematologic malignancies," *Expert Rev. Anticancer Ther.*, 2002, 2(3): 277-286.

Ashida et al., *Rinsho-I*, Oct. 20, 2002, 28(10):2069-71.

Kondo, *Nippon Rinshio*, 1998, 20:69-72, *Bessatsu Rinshobetsu Syokogun*.

Miura, *Gifu-ken Ishikal Igakuzasshi*, 1999, 12(1): 43-7.

Notice of Rejection in corresponding JP Application No. 2004-551395 dated Mar. 15, 2013 (with English summary), translated portion only.

Schey, S.A., "Thalidomide in the Management of Multiple Myeloma", *Hematology*, 2002, 7(5):291-299.

Naika, 1999. 83(1):189-191.

* cited by examiner

METHODS FOR THE TREATMENT OF MYELOPROLIFERATIVE DISEASES USING 4-(AMINO)-2-(2,6-DIOXO(3-PIPERIDYL))-ISOINDOLINE-1,3-DIONE

CROSS-REFERENCE TO RELATED APPLICATION

This application is a divisional application of U.S. patent Application Ser. No. 10/411,656, filed Apr. 11, 2003 now U.S. Pat. No. 7,563,810, which claims priority to U.S. Provisional Patent Application No. 60/424,730 filed on Nov. 6, 2002, the entirety of which is incorporated herein by reference.

FIELD OF THE INVENTION

This invention relates to methods of treating, preventing and/or managing myeloproliferative diseases and related syndromes which comprise the administration of immunomodulatory compounds alone or in combination with other therapies.

BACKGROUND OF THE INVENTION 2.1 Pathobiology of MPD

Myeloproliferative disease (MPD) refers to a group of disorders characterized by clonal abnormalities of the hematopoietic stem cell. See e.g., *Current Medical Diagnosis & Treatment*, pp. 499 (37$^{th}$ ed., Tierney et al. ed, Appleton & Lange, 1998). Since the stem cell gives rise to myeloid, erythroid, and platelet cells, qualitative and quantitative changes can be seen in all these cell lines. Id.

MPD is further subdivided on the basis of the predominantly proliferating myeloid cell type. Erythrocyte excess is classified as "polycythemia rubra vera (PRV)" or "polycythemia vera," platelet excess as "primary (or essential) thrombocythemia (PT)," and granulocyte excess as "chronic myelogenous leukemia (CML)." A fourth subcategory of MPD is "agnogenic myeloid metaplasia (AMM)," which is characterized by bone marrow fibrosis and extramedullary hematopoiesis. *Cecil Textbook of Medicine*, pp. 922 (20$^{th}$ ed., Bennett and Plum ed., W.B. Saunders Company, 1996). These disorders are grouped together because the disease may evolve from one form into another and because hybrid disorders are commonly seen. Tierney et al, supra, at pp. 499. All of the myeloproliferative disorders may progress to acute leukemia naturally or as a consequence of mutagenic treatment. Id.

Most patients with PRV present symptoms related to expanded blood volume and increased blood viscosity. Id. at pp. 500. Common complaints include headache, dizziness, tinnitus, blurred vision, and fatigue. Id. The spleen is palpably enlarged in 75% of cases, but splenomegaly is nearly always present when imaged. Id. Thrombosis is the most common complication of PRV and the major cause of morbidity and death in this disorder. Thrombosis appears to be related to increased blood viscosity and abnormal platelet function. Id. Sixty percent of patients with PRV are male, and the median age at presentation is 60. It rarely occurs in adults under age 40. Id.

Thrombosis is also a common complication in patients suffering from PT. *Cecil Textbook of Medicine*, pp. 922 (20$^{th}$ ed., Bennett and Plum ed., W.B. Saunders Company, 1996). A platelet count ≤6×10$^5$ per microliter has been set to diagnose PT. Tefferi et al., *Mayo Clin Proc* 69:651 (1994). Most patients are asymptomatic when PT is diagnosed, usually through incidental discovery of increased peripheral blood platelet count. Bennett and Plum, supra, at pp. 922. Approximately one quarter, however, have either thrombotic or hemorrhagic events. Id. PT rarely transforms into acute leukemia or AMM, and most patients have a normal life expectancy. Id. at pp. 923. However, at least one third of patients with PT eventually undergo major thrombohemorrhage complications. Id.

AMM is characterized by fibrosis of the bone marrow, splenomegaly, and a leukoerythroblastic peripheral blood picture with teardrop poikilocytosis. Id. at pp. 502. AMM develops in adults over age 50 and is usually insidious in onset. Id. Later in the course of the disease, bone marrow failure takes place as the marrow becomes progressively more fibrotic. Id. Anemia becomes severe. Id. Painful episodes of splenic infarction may occur. Severe bone pain and liver failure also occur in the late stage of AMM. Id. The median survival from time of diagnosis is approximately 5 years. Id. at pp. 503.

The precise cause of MPD is not clear. Current data suggest some growth factors are involved. For instance, in both PRV and PT, in contrast to normal erythroid progenitor cells, polycythemia vera erythroid progenitor cells can grow in vitro in the absence of erythropoietin due to hypersensitivity to insulin like growth factor I. *Harrison's Principles of Internal Medicine*, pp. 701 (15$^{th}$ ed., Braunwald et al. ed., McGraw-Hill, 2001). In AMM, the overproduction of type III collagen has been attributed to platelet-derived growth factor or transforming growth factor β (TGF-β). Id. at pp. 703; see also, Martyr, *Leuk Lymphoma* 6:1 (1991).

In some MPD forms, specific chromosomal changes are seen. For instance, nonrandom chromosome abnormalities, such as 20q-, trisomy 8 or 9 have been documented in a small percentage of untreated PRV patients, and 20q-, 13q-, trisomy Iq are common in AMM patient. *Harrison's Principles of Internal Medicine*, pp. 701-3 (15$^{th}$ ed., Braunwald et al. ed., McGraw-Hill, 2001). Philadelphia chromosome is present in the bone marrow cells of more than 90% of patients with typical CML and some patients with PRV. See e.g., Kurzrock et al., *N Engl J Med* 319:990 (1988). The Philadelphia chromosome results from a balanced translocation of material between the long arms of chromosomes 9 and 22. The break, which occurs at band q34 of the long arm of chromosome 9, allows translocation of the cellular oncogene C-ABL to a position on chromosome 22 called the breakpoint cluster region (bcr). The apposition of these two genetic sequences produces a new hybrid gene (BCR/ABL), which codes for a novel protein of molecular weight 210,000 kD (P210). The P210 protein, a tyrosine kinase, may play a role in triggering the uncontrolled proliferation of CML cells. See e.g., Daley et al., *Science* 247:824 (1990).

The incidence of MPD varies depending on the form of the disease. PRV is diagnosed in 5-17 persons per 1,000,000 per year. *Cecil Textbook of Medicine*, pp. 920-926 (20$^{th}$ ed., Bennett and Plum ed., W.B. Saunders Company, 1996). True incidences of PT and AMM are not known because epidemiological studies on these disorders are inadequate. Id. Internationally, PRV is reportedly lower in Japan, i.e., 2 person per 1,000,000 per year. Id.

2.2 MPD Treatment

The treatment of choice for PRV is phlebotomy. *Current Medical Diagnosis & Treatment*, pp. 501 (37$^{th}$ ed., Tierney et al. ed, Appleton & Lange, 1998). One unit of blood (approximately 500 mL) is removed weekly until the hematocrit is less than 45%. Id. Because repeated phlebotomy produces iron deficiency, the requirement for phlebotomy has to be gradually decreased. Id. It is important to avoid medicinal iron supplementation, as this can thwart the goals of a phlebotomy program. Id.

In more severe cases of PRV, myelosuppressive therapy is used. Id. One of the widely used myelosuppressive agents is hydroxyurea. Id. Hydroxyurea is an oral agent that inhibits ribonucleotide reductase. Bennett and Plum, supra, at pp. 924. The usual dose is 500-1500 mg/d orally, adjusted to keep platelets <500,000/μL without reducing the neurophil count to <2000/μL. Tierney et al, supra, at pp. 501. Side effects of hydroxyurea include mild gastrointestinal complaints, reversible neutropenia, and mucocutaneous lesions. Bennett and Plum, supra, at pp. 924. Busulfan may also be used in a dose of 4-6 mg/d for 4-8 weeks. Tierney et al., supra, at pp. 501. Alpha interferon has been shown to have some ability to control the disease. The usual dose is 2-5 million units subcutaneously three times weekly. Id. Anagrelide has also been approved for use in treatment of thrombocytosis. Id. Some of the myelosuppressive agents, such as alkylating agents and radiophosphorus ($^{32}$P), have been shown to increase the risk of conversion of PRV to acute leukemia. Id. Using myelosuppressive agents for long period may cause prolonged severe myclosuppression.

Most authorities agree that treatment of PT should be aimed at decreasing the level of platelets in patients with a history of thrombosis as well as those with cardiovascular risk factors. Bennett and Plum, supra, at pp. 923. However, the benefit of specific therapy has not been established, and there is concern about the leukemogenic potential of the available therapeutic agents. Id. When treatment is decided upon, the initial drugs are hydroxyurea or anagrelide. Id. at pp. 924. Anagrelide is an oral agent that may involve inhibition of megakaryocyte maturation. Id. The starting dose is 0.5 mg given four times a day. Id. It is relatively contraindicated in elderly patients with heart disease. Id. Alpha interferon can also be used in the treatment of PT. Id.

Currently, there is no specific treatment for AMM. Tierney et al., supra, at pp. 502. The management of AMM is directed to symptoms. Anemic patients are supported with red blood cells in transfusion. Id. Androgens such as oxymetholone, 200 mg orally daily, or testosterone help reduce the transfusion requirement in one third of cases but are poorly tolerated by women. Id. Splenectomy is indicated for splenic enlargement that causes recurrent painful episodes, severe thrombocytopenia, or an unacceptable high red blood cell transfusion requirement. Id. Alpha interferon (2-5 million units subcutaneously three times weekly) leads to improvement in some cases. Id.

Since most therapies used in the treatment of MPD are targeted only at symptoms, and most agents used have serious side effects, with the danger of causing severe myclosuppression or converting the disorder to acute leukemia, there is a great need to find new treatments of MPD that either target the underlying cause of the disorder or improve the effectiveness and safety of the current treatments.

2.3 Thalidomide and Other Compounds Useful in the Treatment of Disease

Thalidomide is a racemic compound sold under the tradename Thalomid® and chemically named α-(N-phthalimido) glutarimide or 2-(2,6-dioxo-3-piperidinyl)-1H-isoindole-1,3 (2H)-dione. Thalidomide was originally developed in the 1950's to treat morning sickness, but due to its teratogenic effects was withdrawn from use. Thalidomide has been approved in the United States for the acute treatment of the cutaneous manifestations of erythema nodosum leprosum in leprosy. Physicians' Desk Reference, 1154-1158 (56$^{th}$ ed., 2002). Because its administration to pregnant women can cause birth defects, the sale of thalidomide is strictly controlled. Id. Thalidomide has reportedly been studied in the treatment of other diseases, such as chronic graft-vs-host disease, rheumatoid arthritis, sarcoidosis, several inflammatory skin diseases, and inflammatory bowel disease. See generally, Koch, H. P., Prog. Med. Chem. 22:165-242 (1985). See also, Moller, D. R., et al., J. Immunol. 159:5157-5161 (1997); Vasiliauskas, E. A., et al., Gastroenterology 117:1278-1287 (1999); Ehrenpreis, E. D., et al., Gastroenterology 117:1271-1277 (1999). It has further been alleged that thalidomide can be combined with other drugs to treat ischemia/repercussion associated with coronary and cerebral occlusion. See U.S. Pat. No. 5,643,915, which is incorporated herein by reference.

More recently, thalidomide was found to exert immunomodulatory and anti-inflammatory effects in a variety of disease states, cachexia in AIDS, and opportunic infections in AIDS. In studies to define the physiological targets of thalidomide, the drug was found to have a wide variety of biological activities exclusive of its sedative effect including neurotoxicity, teratogenicity, suppression of TNF-α production by monocytes/macrophages and the accompanying inflammatory toxicities associated with high levels of TNF-α, and inhibition of angiogenesis and neovascularization.

Additionally, beneficial effects have been observed in a variety of dermatological conditions, ulcerative colitis, Crohn's disease, Bechets's syndrome, systemic lupus erythematosis, aphthous ulcers, and lupus. The anti-angiogenic properties of thalidomide in in vivo models have been reported. D'Amato et al., Thalidomide Is An Inhibitor Of Angiogenesis, 1994, PNAS, USA 91:4082-4085.

One of the most therapeutically significant potential uses of thalidomide is in the treatment of cancer. The compound has been investigated in the treatment of various types of cancer, such as refractory multiple myeloma, brain, breast, colon, and prostate cancer, melanoma, mesothelioma, and renal cell carcinoma. See, e.g., Singhal, S., et al., New England J. Med. 341(21):1565-1571 (1999); and Marx, G. M., et al., Proc. Am. Soc. Clin. Oncology 18:454a (1999). Thalidomide reportedly can also be used to prevent the development of chronic cardiomyopathy in rats caused by doxorubicin. Costa, P. T., et al., Blood 92(10: suppl. 1):235b (1998). Other reports concerning the use of thalidomide in the treatment of specific cancers include its combination with carboplatin in the treatment of glioblastoma multiforne. McCann, J., Drug Topics 41-42 (Jun. 21, 1999). The use of thalidomide in combination with dexamethasone reportedly was effective in the treatment of patients suffering from multiple myeloma who also received, as supportive care, human granulocyte colony-stimulating factor (G-CSF), ciprofloxacin, and non-absorbable antifungal agents. Kropff, M. H., Blood 96(11 part 1):168a (2000); see also, Munshi, N. et al., Blood 94(10 part 1):578a (1999). Other chemotherapy combinations that comprise thalidomide are disclosed in International Application No. PCT/US01/15326 to R. Govindarjan and A. Zeitlan, and in International Application No. PCT/US01/15327 to J. B. Zeldis, et al.

In an effort to provide compounds that have greater therapeutic safety and efficacy than thalidomide, researchers have begun investigating a large number of other compounds, some of which are derivatives of thalidomide. See, e.g., Marriott, J. B., et al., Expert Opin. Biol. Ther. 1(4):1-8 (2001); G. W. Muller, et al., Journal of Medicinal Chemistry 39(17): 3238-3240 (1996); and G. W. Muller, et al., Bioorganic & Medicinal Chemistry Letters 8:2669-2674 (1998). Examples include, but are not limited to, the substituted 2-(2,6-dioxopiperidin-3-yl)phthalimies and substituted 2-(2,6-dioxopiperidin-3-yl)-1-oxoisoindoles described in U.S. Pat. Nos. 6,281,230 and 6,316,471, both to G. W. Muller, et al.

A group of compounds selected for their capacity to potently inhibit TNF-α production by LPS stimulated PBMC has been investigated. L. G. Corral, et al., Ann. Rheum. Dis. 58: (SupplI) 1107-1113 (1999). These compounds, which are referred to as IMiDs™ or Immunomodulatory Drugs, show not only potent inhibition of TNF-α but also marked inhibition of LPS induced monocyte IL1β and IL12 production. LPS induced IL6 is also inhibited by IMiDs™, albeit partially. These compounds are potent stimulators of LPS induced IL10, increasing IL10 levels by 200 to 300%. Id.

While many such compounds have shown promise as therapeutic agents, their mechanisms of action and effectiveness are still under investigation. Moreover, there remains a need for therapeutic agents to treat MPD and its related disorders.

SUMMARY OF THE INVENTION

This invention encompasses methods of treating and preventing myeloproliferative disease ("MPD") which comprise administering to a patient in need thereof a therapeutically or prophylactically effective amount of an immunomodulatory compound of the invention, or a pharmaceutically acceptable salt, solvate, hydrate, stereoisomer, clathrate, or prodrug thereof. The invention also encompasses methods of managing MPD (e.g., lengthening the time of remission) which comprise administering to a patient in need of such management a therapeutically or prophylactically effective amount of an immunomodulatory compound of the invention, or a pharmaceutically acceptable salt, solvate, hydrate, stereoisomer, clathrate, or prodrug thereof.

One embodiment of the invention encompasses the use of one or more immunomodulatory compounds in combination with conventional therapies presently used to treat, prevent or manage MPD such as, but not limited to, hydroxyurea, anagrelide, interferons, kinase inhibitors, cancer chemotherapeutics, stem cell transplantation and other transplantations.

Another embodiment of the invention encompasses a method of reducing or preventing an adverse effect associated with MPD therapy, which comprises administering to a patient in need of such treatment or prevention an amount of an immunomodulatory compound of the invention, or a pharmaceutically acceptable salt, solvate, hydrate, stereoisomer, clathrate, or prodrug thereof, that is sufficient to reduce an adverse effect associated with the MPD therapy. This embodiment includes the use of an immunomodulatory compound of the invention to protect against or treat an adverse effect associated with the use of the MPD therapy. This embodiment encompasses raising a patient's tolerance for the MPD therapy.

Another embodiment of the invention encompasses a method of increasing the therapeutic efficacy of a MPD treatment which comprises administering to a patient in need of such increased therapeutic efficacy an amount of an immunomodulatory compound of the invention, or a pharmaceutically acceptable salt, solvate, hydrate, stereoisomer, clathrate, or prodrug thereof, that is sufficient to increase the therapeutic efficacy of the MPD treatment.

The invention further encompasses pharmaceutical compositions, single unit dosage forms, and kits suitable for use in treating, preventing and/or managing MPD, which comprise an immunomodulatory compound of the invention, or a pharmaceutically acceptable salt, solvate, hydrate, stereoisomer, clathrate, or prodrug thereof.

DETAILED DESCRIPTION OF THE INVENTION

A first embodiment of the invention encompasses methods of treating or preventing MPD, which comprise administering to a patient in need of such treatment or prevention a therapeutically or prophylactically effective amount of an immunomodulatory compound or a pharmaceutically acceptable salt, solvate, hydrate, stereoisomer, clathrate, or prodrug thereof. The embodiment encompasses the treatment, prevention or management of specific sub-types of MPD such as, but not limited to, polycythemia rubra vera (PRV), primary thrombocythemia (PT), and agnogenic myeloid metaplasia (AMM).

As used herein, the term "myeloproliferative disease," or "MPD," means a hematopoietic stem cell disorder characterized by one or more of the following: clonal expansion of a multipotent hematopoietic progenitor cell with the overproduction of one or more of the formed elements of the blood (e.g., elevated red blood cell count, elevated white blood cell count, and/or elevated platelet count), presence of Philadelphia chromosome or bcr-abl gene, teardrop poikilocytosis on peripheral blood smear, leukoerythroblastic blood pictuer, giant abnormal platelets, hypercellular bone marrow with reticular or collagen fibrosis, marked left-shifted myeloid series with a low percentage of promyelocytes and blasts, splenomegaly, thrombosis, risk of progression to acute leukemia or cellular marrow with impaired morphology. The term "myeloproliferative disease," or "MPD," unless otherwise noted includes: polycythemia rubra vera (PRV), primary thrombocythemia (PT), and agnogenic myeloid metaplasia (AMM). In a specific embodiment, the term "myeloproliferative disease" or "MPD" excludes leukemia. Particular types of MPD are PRV, PT, and AMM.

Another embodiment of the invention encompasses methods of managing MPD which comprises administering to a patient in need of such management a prophylactically effective amount of an immunomodulatory compound or a pharmaceutically acceptable salt, solvate, hydrate, stereoisomer, clathrate, or prodrug thereof.

Another embodiment of the invention encompasses a pharmaceutical composition comprising an immunomodulatory compound or a pharmaceutically acceptable salt, solvate, hydrate, stereoisomer, clathrate, or prodrug thereof.

Also encompassed by the invention are single unit dosage forms comprising an immunomodulatory compound or a pharmaceutically acceptable salt, solvate, hydrate, stereoisomer, clathrate, or prodrug thereof.

Another embodiment of the invention encompasses a method of treating, preventing and/or managing MPD, which comprises administering to a patient in need of such treatment, prevention and/or management a therapeutically or prophylactically effective amount of an immunomodulatory compound or a pharmaceutically acceptable salt, solvate, hydrate, stereoisomer, clathrate, or prodrug thereof, and a therapeutically or prophylactically effective amount of a second active agent.

Examples of second active agents include, but are not limited to, cytokines, corticosteroids, ribonucleotide reductase inhibitors, platelet inhibitors, all-trans retinoic acids, kinase inhibitors, topoisomerase inhibitors, farnesyl transferase inhibitors, antisense oligonucleotidcs, vaccines, anti-cancer agents, anti-fungal agents, anti-inflammatory agents, immunosuppressive or myelosuppressive agents, and conventional therapies for MPD.

Without being limited by theory, it is believed that certain immunomodulatory compounds of the invention can act in complementary or synergistic ways with conventional and other therapies in the treatment or management of MPD. It is also believed that certain immunomodulatory compounds of the invention act by different mechanisms than conventional and other therapies in the treatment or management of MPD. In addition, it is believed that certain immunomodulatory compounds of the invention are effective when administered to patients who are refractory to conventional treatments for myeloproliferative diseases as well as treatments using thalidomide. As used herein, the term "refractory" means the patient's response to a MPD treatment is not satisfactory by clinical standards, e.g., show no or little improvement of symptoms or laboratory findings.

It is also believed that certain therapies may reduce or eliminate particular adverse effects associated with some immunomodulatory compounds, thereby allowing the administration of larger amounts of an immunomodulatory compound to patients and/or increasing patient compliance. It is further believed that some immunomodulatory compounds may reduce or eliminate particular adverse effects associated with other MPD therapies, thereby allowing the administration of larger amounts of such therapies to patients and/or increasing patient compliance.

Another embodiment of the invention encompasses a kit comprising: a pharmaceutical composition comprising an immunomodulatory compound of the invention, or a pharmaceutically acceptable salt, solvate, hydrate, stereoisomer, clathrate, or prodrug thereof and a second active agent and/or instructions for use. The invention further encompasses kits comprising single unit dosage forms.

Another embodiment of the invention encompasses a method of reversing, reducing or avoiding an adverse effect associated with the administration of an active agent used to treat MPD in a patient suffering from MPD, which comprises administering to a patient in need thereof a therapeutically or prophylactically effective amount of an immunomodulatory compound or a pharmaceutically acceptable salt, solvate, hydrate, stereoisomer, clathrate, or prodrug thereof. Examples of active agents include, but are not limited to, the second active agents described herein (see section 4.2.).

Examples of adverse effects associated with active agents used to treat MPD include, but are not limited to: conversion to acute leukemia; severe myelosuppression; gastrointestinal toxicity such as, but not limited to, early and late-forming diarrhea and flatulence; gastrointestinal bleeding; nausea; vomiting; anorexia; leukopenia; anemia; neutropenia; asthenia; abdominal cramping; fever; pain; loss of body weight; dehydration; alopecia; dyspnea; insomnia; dizziness, mucositis, xerostomia, mucocutaneous lesions, and kidney failure.

As leukemic transformation develops in certain stages of MPD, transplantation of peripheral blood stem cells, hematopoietic stem cell preparation or bone marrow may be necessary. Without being limited by theory, it is believed that the combined use of an immunomodulatory compound and the transplantation of stem cells in a patient suffering from MPD provides a unique and unexpected synergism. In particular, it is believed that certain immunomodulatory compounds of the invention exhibit immunomodulatory activity that can provide additive or synergistic effects when given concurrently with transplantation therapy. Immunomodulatory compounds of the invention can work in combination with transplantation therapy to reduce complications associated with the invasive procedure of transplantation and risk of related Graft Versus Host Disease (GVHD). Therefore, this invention encompasses a method of treating, preventing and/or managing MPD, which comprises administering to a patient (e.g., a human) an immunomodulatory compound of the invention, or a pharmaceutically acceptable salt, solvate, hydrate, stereoisomer, clathrate, or prodrug thereof, before, during, or after transplantation therapy.

The invention also encompasses pharmaceutical compositions, single unit dosage forms, and kits which comprise one or more immunomodulatory compounds or a pharmaceutically acceptable salt, solvate, hydrate, stereoisomer, clathrate, or prodrug thereof, a second active ingredient, and/or blood or cells for transplantation therapy. For example, a kit may contain one or more compounds of the invention, stem cells for transplantation and an immunosuppressive agent, and an antibiotic or other drug.

4.1 Immunomodulatory Compounds

Compounds used in the invention include immunomodulatory compounds that are racemic, stereomerically enriched or stereomerically pure, and pharmaceutically acceptable salts, solvates, hydrates, stereoisomers, clathrates, and prodrugs thereof. Preferred compounds used in the invention are small organic molecules having a molecular weight less than about 1000 g/mol, and are not proteins, peptides, oligonucleotides, oligosaccharides or other macromolecules.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

As used herein and unless otherwise indicated, the term "immunomodulatory compounds" or "IMiDs™" (Celgene Corporation) used herein encompasses small organic molecules that markedly inhibit TNF-α, LPS induced monocyte IL1β and IL12, and partially inhibit IL6 production. Specific immunomodulatory compounds of the invention are discussed below.

TNF-α is an inflammatory cytokine produced by macrophages and monocytes during acute inflammation. TNF-α is responsible for a diverse range of signaling events within cells. TNF-α may play a pathological role in cancer. Without being limited by particular theory, one of the biological effects exerted by the immunomodulatory compounds of the invention is the reduction of synthesis of TNF-α Immunomodulatory compounds of the invention enhance the degradation of TNF-α mRNA.

Further, without being limited by particular theory, immunomodulatory compounds used in the invention may also be potent co-stimulators of T cells and increase cell proliferation dramatically in a dose dependent manner. Immunomodulatory compounds of the invention may also have a greater co-stimulatory effect on the CD8+ T cell subset than on the CD4+ T cell subset. In addition, the compounds preferably have anti-inflammatory properties, and efficiently co-stimulate T cells.

Specific examples of immunomodulatory compounds of the invention, include, but are not limited to, cyano and carboxy derivatives of substituted styrenes such as those disclosed in U.S. Pat. No. 5,929,117; 1-oxo-2-(2,6-dioxo-3-fluoropiperidin-3yl) isoindolines and 1,3-dioxo-2-(2,6-dioxo-3-fluoropiperidine-3-yl) isoindolines such as those described in U.S. Pat. No. 5,874,448; the tetra substituted 2-(2,6-dioxopiperdin-3-yl)-1-oxoisindolines described in U.S. Pat. No. 5,798,368; 1-oxo and 1,3-dioxo-2-(2,6-dioxopiperidin-3-yl) isoindolines (e.g., 4-methyl derivatives of thalidomide and EM-12), including, but not limited to, those disclosed in U.S. Pat. No. 5,635,517; and a class of nonpolypeptide cyclic amides disclosed in U.S. Pat. Nos. 5,698,579 and 5,877,200; analogs and derivatives of thalidomide, including hydrolysis products, metabolites, derivatives and precursors of thalidomide, such as those described in U.S. Pat. Nos. 5,593,990, 5,629,327, and 6,071,948 to D'Amato; aminothalidomide, as well as analogs, hydrolysis products, metabolites, derivatives and precursors of aminothalidomide, and substituted 2-(2,6-dioxopiperidin-3-yl) phthalimides and substituted 2-(2,6-dioxopiperidin-3-yl)-1-oxoisoindoles such as those described in U.S. Pat. Nos. 6,281,230 and 6,316,471; isoindole-imide compounds such as those described in U.S. patent application Ser. No. 09/972,487 filed on Oct. 5, 2001, U.S. patent application Ser. No. 10/032,286 filed on Dec. 21, 2001, and International Application No. PCT/US01/50401 (International Publication No. WO 02/059106). The entireties of each of the patents identified herein are incorporated herein by reference. Immunomodulatory compounds of the invention do not include thalidomide.

Other specific immunomodulatory compounds of the invention include, but are not limited to, 1-oxo-and 1,3 dioxo-2-(2,6-dioxopiperidin-3-yl) isoindolines substituted with amino in the benzo ring as described in U.S. Pat. No. 5,635,517 which is incorporated herein. These compounds have the structure I:

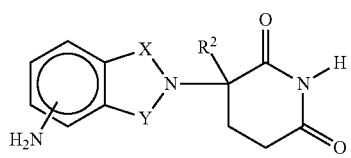

in which one of X and Y is C=O, the other of X and Y is C=O or CH$_2$, and R$^2$ is hydrogen or lower alkyl, in particular methyl. Specific immunomodulatory compounds include, but are not limited to:

1-oxo-2-(2,6-dioxopiperidin-3-yl)-4-aminoisoindoline;
1-oxo-2-(2,6-dioxopiperidin-3-yl)-5-aminoisoindoline;
1-oxo-2-(2,6-dioxopiperidin-3-yl)-6-aminoisoindoline;
1-oxo-2-(2,6-dioxopiperidin-3-yl)-7-aminoisoindoline;
1,3-dioxo-2-(2,6-dioxopiperidin-3-yl)-4-aminoisoindoline;
and 1,3-dioxo-2-(2,6-dioxopiperidin-3-yl)-5-aminoisoindoline.

Other specific immunomodulatory compounds of the invention belong to a class of substituted 2-(2,6-dioxopiperidin-3-yl) phthalimides and substituted 2-(2,6-dioxopiperidin-3-yl)-1-oxoisoindoles, such as those described in U.S. Pat. Nos. 6,281,230; 6,316,471; 6,335,349; and 6,476,052, and International Patent Application No. PCT/US97/13375 (International Publication No. WO 98/03502), each of which is incorporated herein. Compounds representative of this class are of the formulas:

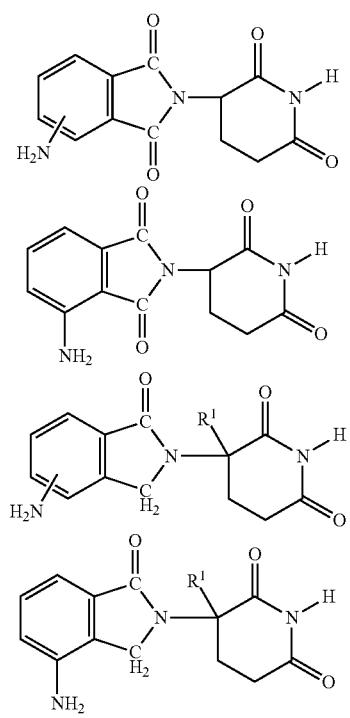

wherein R$^1$ is hydrogen or methyl. In a separate embodiment, the invention encompasses the use of enantiomerically pure forms (e.g. optically pure (R) or (S) enantiomers) of these compounds.

Still other specific immunomodulatory compounds of the invention belong to a class of isoindole-imides disclosed in U.S. patent application Ser. Nos. 10/032,286 and 09/972,487, and International Application No. PCT/US01/50401(International Publication No. WO 02/059106), each of which are incorporated herein by reference. Representative compounds are of formula II:

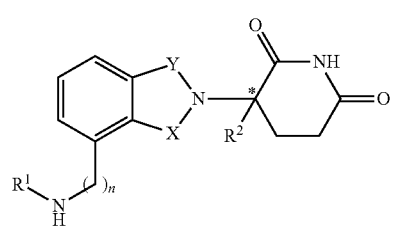

and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;

$R^1$ is H, $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$C_1-C_6)$heterocycloalkyl, $(C_0-C_4)$alkyl-$(C_2-C_5)$heteroaryl, C(O)$R^3$, C(S)$R^3$, C(O)O$R^4$, $(C_1-C_8)$alkyl-N($R^6$)$_2$, $(C_1-C_8)$alkyl-O$R^5$, $(C_1-C_8)$alkyl-C(O)O$R^5$, C(O)NH$R^3$, C(S)NH$R^3$, C(O)N$R^3R^{3'}$, C(S)N$R^3R^{3'}$ or $(C_1-C_8)$alkyl-O(CO)$R^5$;

$R^2$ is H, F, benzyl, $(C_1-C_8)$alkyl, $(C_2-C_8)$alkenyl, or $(C_2-C_8)$alkynyl;

$R^3$ and $R^{3'}$ are independently $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_0-C_8)$alkyl-N($R^6$)$_2$, $(C_1-C_8)$alkyl-O$R^5$, $(C_1-C_8)$alkyl-C(O)O$R^5$, $(C_1-C_8)$alkyl-O(CO)$R^5$, or C(O)O$R^5$;

$R^4$ is $(C_1-C_8)$alkyl, $(C_2-C_8)$alkenyl, $(C_2-C_8)$alkynyl, $(C_1-C_4)$alkyl-O$R^5$, benzyl, aryl, $(C_0-C_4)$alkyl-$(C_1-C_6)$heterocycloalkyl, or $(C_0-C_4)$alkyl-$(C_2-C_5)$heteroaryl;

$R^5$ is $(C_1-C_8)$alkyl, $(C_2-C_8)$alkenyl, $(C_2-C_8)$alkynyl, benzyl, aryl, or $(C_2-C_5)$heteroaryl;

each occurrence of $R^6$ is independently H, $(C_1-C_8)$alkyl, $(C_2-C_8)$alkenyl, $(C_2-C_8)$alkynyl, benzyl, aryl, $(C_2-C_5)$heteroaryl, or $(C_0-C_8)$alkyl-C(O)O—$R^5$ or the $R^6$ groups can join to form a heterocycloalkyl group;

n is 0 or 1; and

\* represents a chiral-carbon center.

In specific compounds of formula II, when n is 0 then R1 is (C3-C7)cycloalkyl, (C2-C8)alkenyl, (C2-C8)alkynyl, benzyl, aryl, (C0-C4)alkyl-(C1-C6)heterocycloalkyl, (C0-C4)alkyl-(C2-C5)heteroaryl, C(O)R3, C(O)OR4, (C1-C8)alkyl-N(R6)2, (C1-C8)alkyl-OR5, (C1-C8)alkyl-C(O)OR5, C(S)NHR3, or (C1-C8)alkyl-O(CO)R5;

$R^2$ is H or $(C_1-C_8)$alkyl; and $R^3$ is $(C_1-C_8)$alkyl, $(C_3-C_7)$cycloalkyl, $(C_2-C_8)$alkenyl, $(C_2-C8)$alkynyl, benzyl, aryl, $(C_0-C_4)$alkyl-$C_1-C_6)$heterocycloalkyl, $(C_0-C_4)$alkyl-$C_2-C_5)$heteroaryl, $(C_5-C_8)$alkyl-N($R^6$)$_2$; $(C_0-C_8)$alkyl-NH—C(O)O—$R^5$; $(C_1-C_8)$alkyl-O$R^5$, $(C_1-C_8)$alkyl-C(O)O$R^5$, $(C_1-C_8)$alkyl-O(CO)$R^5$, or C(O)O$R^5$; and the other variables have the same definitions.

In other specific compounds of formula II, $R^2$ is H or $(C_1-C_4)$alkyl.

In other specific compounds of formula II, $R^1$ is $(C_1-C_8)$ alkyl or benzyl.

In other specific compounds of formula II, $R^1$ is H, $(C_1-C_8)$alkyl, benzyl, $CH_2OCH_3$, $CH_2CH_2OCH_3$, or

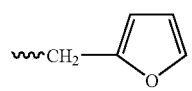

In another embodiment of the compounds of formula II, $R^1$ is

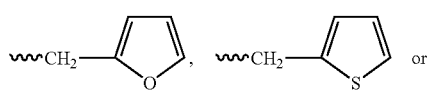

-continued

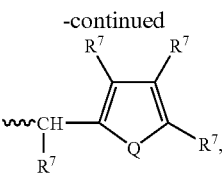

wherein Q is O or S, and each occurrence of $R^7$ is independently H, $(C_1-C_8)$alkyl, benzyl, $CH_2OCH_3$, or $CH_2CH_2OCH_3$.

In other specific compounds of formula II, $R^1$ is C(O)$R^3$.

In other specific compounds of formula II, $R^3$ is $(C_0-C_4)$ alkyl-$(C_2-C_5)$heteroaryl, $(C_1-C_8)$alkyl, aryl, or $(C_0-C_4)$alkyl-O$R^5$.

In other specific compounds of formula II, heteroaryl is pyridyl, furyl, or thienyl.

In other specific compounds of formula II, $R^1$ is C(O)O$R^4$.

In other specific compounds of formula II, the H of C(O) NHC(O) can be replaced with $(C_1-C_4)$alkyl, aryl, or benzyl.

Still other specific immunomodulatory compounds of the invention belong to a class of isoindole-imides disclosed in U.S. patent application Ser. No. 09/781,179, International Publication No. WO 98/54170, and U.S. Pat. No. 6,395,754, each of which are incorporated herein by reference. Representative compounds are of formula III:

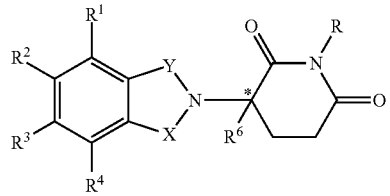

and pharmaceutically acceptable salts, hydrates, solvates, clathrates, enantiomers, diastereomers, racemates, and mixtures of stereoisomers thereof, wherein:

one of X and Y is C=O and the other is $CH_2$ or C=O;

R is H or CH2OCOR';

(i) each of $R^1$, $R^2$, $R^3$, or $R^4$, independently of the others, is halo, alkyl of 1 to 4 carbon atoms, or alkoxy of 1 to 4 carbon atoms or (ii) one of $R^1$, $R^2$, $R^3$, or $R^4$ is nitro or —NH$R^5$ and the remaining of $R^1$, $R^2$, $R^3$, or $R^4$ are hydrogen;

$R^5$ is hydrogen or alkyl of 1 to 8 carbons $R^6$ hydrogen, alkyl of 1 to 8 carbon atoms, benzo, chloro, or fluoro;

R' is $R^7$—CHR$^{10}$—N($R^8R^9$);

$R^7$ is m-phenylene or p-phenylene or —$(C_nH_{2n})$— in which n has a value of 0 to 4;

each of R8 and R9 taken independently of the other is hydrogen or alkyl of 1 to 8 carbon atoms, or R8 and R9 taken together are tetramethylene, pentamethylene, hexamethylene, or —$CH_2CH_2[X]X_1CH_2CH_2$— in which [X]$X_1$ is —O—, —S—, or —NH—;

$R^{10}$ is hydrogen, alkyl of to 8 carbon atoms, or phenyl; and

\* represents a chiral-carbon center.

The most preferred immunomodulatory compounds of the invention are 4-(amino)-2-(2,6-dioxo(3-piperidyl))-isoindoline-1,3-dione and 3-(4-amino-1-oxo-1,3-dihydro-isoindol-2-yl)-piperidine-2,6-dione. The compounds can be obtained via standard, synthetic methods (see e.g., U.S. Pat. No. 5,635, 517, incorporated herein by reference). The compounds are available from Celgene Corporation, Warren, N.J.

4-(Amino)-2-(2,6-dioxo(3-piperidyl))-isoindoline-1,3-dione (ACTIMID™) has the following chemical structure:

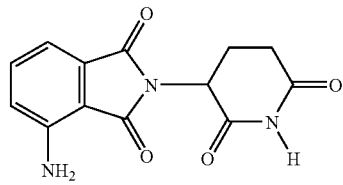 [SMILES: Nc1cccc2c1C(=O)N(C1CCC(=O)NC1=O)C2=O]

3-(4-amino-1-oxo-1,3-dihydro-isoindol-2-yl)-piperidine-2,6-dione (REVIMID™) has the following chemical structure:

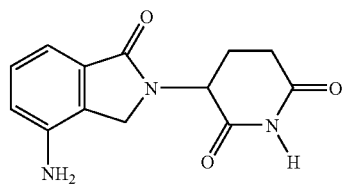 [SMILES: Nc1cccc2c1CN(C1CCC(=O)NC1=O)C2=O]

The compounds of the invention can either be commercially purchased or prepared according to the methods described in the patents or patent publications disclosed herein. Further, optically pure compounds can be asymmetrically synthesized or resolved using known resolving agents or chiral columns as well as other standard synthetic organic chemistry techniques.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of immunomodulatory compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of immunomodulatory compounds of the invention that comprise —NO, —NO$_2$, —ONO, or —ONO$_2$ moieties. Prodrugs can typically be prepared using well-known methods, such as those described in 1 *Burger's Medicinal Chemistry and Drug Discovery*, 172-178, 949-982 (Manfred E. Wolff ed., 5th ed. 1995), and *Design of Prodrugs* (H. Bundgaard ed., Elselvier, New York 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyloxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, aminoacids, hydroxyalkylamines, heterocyclic and heteroaromatic amines, and polyether amines.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

4.2 Second Active Agents

One or more active ingredients can be used in combination with an immunomodulatory compound of the present invention. Preferably, the second active ingredient, or agent, is capable of suppressing the overproduction of hematopoietic stem cells, or ameliorating one or more of the symptoms of MPD.

Second active agents can be, but are not limited to, small molecules (e.g., synthetic inorganic, organometallic, or organic molecules), large molecules, synthetic drugs, peptides, polypeptides, proteins, nucleic acids, antibodies and the like. Any agent that is known to be useful, or that has been used or is currently being used for the prevention, treatment or amelioration of one or more symptoms of MPD can be used in the combination with the present invention. Particular agents include, but are not limited to, anticancer agents (e.g., antimetabolites, antibiotics, alkylating agents, microtubule inhibitors, steroid hormones, DNA-repair enzyme inhibitors, kinase inhibitors, farnesyl transferase inhibitors, antisense oligonucleotides, immunomodulators, antibodies, vaccines, and adnosine deaminase inhibitors), all-trans retinoic acid (e.g., arsenic trioxide), platelet inhibitors (e.g., aspirin, dipyridamole, ticlopidine, anagrelide), anticoagulants (e.g., enoxaprin, heparin, warfarin), thrombolytic agents (e.g., alteplase (tPA), anistreplase, streptokinase, urokinase), antifibrosis agents (e.g., penicillamine, suramin, clochicine), agents used in treating bleeding (e.g., aminocaproic acid, protamine sulfate, vitamin K), and agents used in treating anemia (e.g., vitamin K, folic acid).

This invention also encompasses the use of native, naturally occurring, and recombinant proteins. The invention further encompasses mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

This invention further encompasses the use of immune cells or transplantation of blood and marrow stem cells. For example, CML patients can be treated with infusion of donor white blood cells that suppress the growth of leukemia cells. Slavin et al., *Transfus Apheresis Sci* 27(2): 159-66 (2002).

Examples of anti-cancer drugs that can be used in the various embodiments of the invention, including the methods, dosing regimens, cocktails, pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethan immunomodulatory compound of the inventione; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; dacarbazine; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletan immunomodulatory compound of the inventione; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorlns; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; an immunomodulatory compound of the inventionazacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptoistatin; letrozole; leukemia inhibiting factor; leukocyte alpha interferon; leuprolide+estrogen+ progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; $O^6$-benzylguanine; oblimersen; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletan immunomodulatory compound of the inventione; rohitukine; romurtide; roquinimex; rubiginone B1; ruboxyl; safiingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoictin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred anti-cancer drugs are those that have been shown to have treatment benefit in a MPD patient, e.g., interferon-α, hydroxyurea, busulfan, anagrelide, daunorubicin, cincristine, corticosteroid hormones (e.g., prednisone, beclomethasone, cortisone, dexamethasone, fludrocortisone, hydrocortisone, methylprednisolone), kinase inhibitors, topoisomerase inhibitors, farnesyl transferase inhibitors, vaccines and antisense nucleotides.

Examples of kinase inhibitors include, but are not limited to, compound ST1571, imatinib mesylate (Kantarjian et al., *Clin Cancer Res.* 8(7):2167-76 (2002)), and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223,5,863,904, 5,840,745, 5,728,868, 5,648,239, 5,587,459, all of which are incorporated herein by reference. Preferred kinase inhibitors include, but are not limited to, those that directly target the BCR/ABL kinase or other kinases that are involved in the MPD pathophysiology, e.g., ST1571, and imatinib mesylate.

Examples of topoisomerase inhibitors include, but are not limited to, camptothecin; irinotecan; SN-38; topotecan; 9-aminocamptothecin; GG-211 (GI 147211); DX-8951f; IST-622; rubitecan; pyrazoloacridine; XR-5000; saintopin; UCE6; UCE1022; TAN-1518A; TAN-1518B; KT6006; KT6528; ED-110; NB-506; ED-110; NB-506; and rebeccamycin; bulgarein; DNA minor groove binders such as Hoescht dye 33342 and Hoechst dye 33258; nitidine; fagaronine; epiberberine; coralyne; beta-lapachone; BC-4-1; and pharmaceutically acceptable salts, solvates, clathrates, and prodrugs thereof. See, e.g., Rothenberg, M. L., *Annals of Oncology* 8:837-855(1997); and Moreau, P., et al., *J. Med. Chem.* 41:1631-1640(1998). Examples of camptothecin derivatives that can be used in the methods and compositions of this invention are disclosed by, for example, U.S. Pat. Nos. 6,043,367; 6,040,313; 5,932,588; 5,916,896; 5,889,017; 5,801,167; 5,674,874; 5,658,920; 5,646,159; 5,633,260; 5,604,233; 5,597,829; 5,552,154; 5,541,327; 5,525,731; 5,468,754; 5,447,936; 5,446,047; 5,401,747; 5,391,745; 5,364,858; 5,340,817; 5,244,903; 5,227,380; 5,225,404; 5,180,722; 5,122,606; 5,122,526; 5,106,742; 5,061,800; 5,053,512; 5,049,668; 5,004,758; 4,981,968; 4,943,579; 4,939,255; 4,894,456; and 4,604,463, each of which is incorporated herein by reference. Preferred topoisomerase inhibitors include, but are not limited to, DX-8951f, irinotccan, SN-38, and pharmaceutically acceptable salts, solvates, clathrates, and prodrugs thereof.

Examples of famesyl transferase inhibitor include, but are not limited to, R115777, BMS-214662, (for review, see Caponigro, *Anticancer Drugs* 13(8):891-897 (2002)), and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, 6,040,305, all of which are incorporated herein by reference.

In one embodiment of the present invention, the second active agent is an agent used in the gene therapy of MPD. For example, antisense oligonucleotides can block the encoding instructions of an oncogene so that it cannot direct the formation of the corresponding oncoprotein that causes the cell to transform into a malignant cell. Examples of antisense oligonucleotides include, but are not limited to, those disclosed in the U.S. Pat. Nos. 6,277,832, 5,998,596, 5,885,834, 5,734,033, and 5,618,709, all of which are incorporated herein by reference.

In another embodiment of the present invention, the second active agent is a protein, a fusion protein thereof, or a vaccine that secretes the protein, wherein the protein is IL-2, IL-10, IL-12, IL18, G-CSF, GM-CSF, EPO, or a pharmacologically active mutant or derivative thereof. In some circumstances apparent to one skilled in the art, G-CSF, GM-CSF and EPO are not preferred. For example, G-CSF, GM-CSF and EPO preferably are not used in methods that do not utilize stem cell transplantation. In a preferred embodiment, the protein is an antibody or an antibody linked to a chemical toxin or radioactive isotope that targets and kills specific overproduced cells in a MPD patient. Such antibodies include, but are not limited to, rituximab (Rituxan®), calicheamycin (Mylotarg®), ibritumomab tiuxetan (Zevalin®), and tositumomab (Bexxar®).

In a specific embodiment of the present invention, the second active agent is a vaccine that can induce antigen-specific anti-malignant cell immune responses in a MPD patient. A non-limiting example of such a vaccine is disclosed in U.S. Pat. No. 6,432,925, which is incorporated herein by reference.

In yet another embodiment of the present invention, the second active agent is one that is capable of reversal of multidrug resistance in MPD patients. The overproduced cells in MPD patients have mechanisms that may allow them to escape the damaging effects of chemotherapy. New agents are being studied to decrease resistance to an important chemotherapeutic drug used in the treatment of leukemia. Non-limiting examples of such agents are disclosed in U.S. Pat. No. 6,225,325, which is incorporated herein by reference.

Other agents that can be used in combination with the present invention include, but are not limited to, those disclosed in U.S. Pat. Nos. 6,096,300, 6,420,391, 6,326,205, 5,866,332, 6,458,349, 6,420,378, 6,399,664, 6,395,771, 6,346,246, 6,333,309, 6,331,642, 6,329,497, 6,326,378, 6,313,129, 6,306,393, 6,303,646, 6,265,427, 6,262,053, 6,258,779, 6,251,882, 6,231,893, 6,225,323, 6,221,873, 6,218,412, 6,204,364, 6,187,287, 6,183,988, 6,183,744, 6,172,112, 6,156,733, 6,143,738, 6,127,406, 6,121,320, 6,107,520, 6,107,457, 6,075,015, and 6,063,814, all of which are incorporated herein by reference.

4.3 Methods of Treatment and Management

Methods of this invention encompass methods of preventing, treating and/or managing various types of MPD. As used herein, unless otherwise specified, the terms "treating" and "preventing" encompass the inhibition or the reduction of the severity or magnitude of one or more symptoms or laboratory findings associated with MPD. Symptoms associated with MPD include, but are not limited to, headache, dizziness, tinnitus, blurred vision, fatigue, night sweat, low-grade fever, generalized pruritus, epistaxis, blurred vision, splenomegaly, abdominal fullness, thrombosis, increased bleeding, anemia, splenic infarction, severe bone pain, hematopoiesis in the liver, ascites, esophageal varices, liver failure, respiratory distress, and priapism. Laboratory findings associated with MPD include, but are not limited to, clonal expansion of a multipotent hematopoietic progenitor cell with the overproduction of one or more of the formed elements of the blood (e.g., elevated red blood cell count, elevated white blood cell count, and/or elevated platelet count), presence of Philadelphia chromosome or bcr-abl gene, teardrop poikilocytosis on peripheral blood smear, leukoerythroblastic blood pictuer, giant abnormal platelets, hypercellular bone marrow with reticular or collagen fibrosis, and marked left-shifted myeloid series with a low percentage of promyelocytes and blasts. As used herein, unless otherwise specified, the term "treating" refers to the administration of a composition after the onset of symptoms of MPD, whereas "preventing" refers to the administration prior to the onset of symptoms, particularly to patients at risk of MPD. As used herein and unless otherwise indicated, the term "managing" encompasses preventing the recurrence of MPD in a patient who had suffered from MPD, lengthening the time a patient who had suffered from MPD remains in remission, and/or preventing the occurrence of MPD in patients at risk of suffering from MPD.

The invention encompasses methods of treating or preventing patients with primary and secondary MPD. It further encompasses methods treating patients who have been previously treated for MPD, as well as those who have not previously been treated for MPD. Because patients with MPD have heterogenous clinical manifestations and varying clinical outcomes, it has become apparent that staging the patients according to their prognosis and approaching therapy depending on the severity and stage may be necessary. Indeed, the methods and compositions of this invention can be used in various stages of treatments for patients with one or more types of MPD including, but not limited to, polycythemia rubra vera (PRV), primary thromobocythemia (PT), and agnogenic myeloid metaplasia (AMM).

Methods encompassed by this invention comprise administering an immunomodulatory compound of the invention, or a pharmaceutically acceptable salt, solvate, hydrate, stereoisomer, clathrate, or prodrug thereof to a patient (e.g., a human) suffering, or likely to suffer, from MPD. Specific patient populations include the elderly, i.e., ages 60 and above as well as those over 35 years of age. Patients with familial history of MPD or leukemia are also preferred candidates for preventive regimens.

In one embodiment of the invention, an immunomodulatory compound of the invention is administered orally and in a single or divided daily doses in an amount of from about 0.10 to about 150 mg/day. In a particular embodiment, 4-(amino)-2-(2,6-dioxo(3-piperidyl))-isoindoline-1,3-dione (Actimid™) is administered in an amount of from about 0.1 to about 5 mg per day. Or about 0.1 to about 1 mg per day, or alternatively from about 1 to about 10 mg every other day, or about 5 mg every other day.

3-(4-Amino-1-oxo-1,3-dihydro-isoindol-2-yl)-piperidine-2,6-dione (Revimid™) can be preferably administered in an amount of from about 2.5 to about 25 mg per day. Or about 5 mg to about 10 mg per day, or alternatively from about 5 to about 50 mg every other day, or about 10 to about 20 mg every other day. Other dosing regimens for the compounds will be apparent to the skilled artisan and may involve other dosing schedules known in the art such as, but not limited to, one week of daily therapy with the compounds of the invention followed by one week off.

4.3.1 Combination Therapy with a Second Active Agent

Particular methods of the invention comprise administering 1) an immunomodulatory compound or a pharmaceutically acceptable salt, solvate, hydrate, stereoisomer, clathrate, or prodrug thereof, and 2) a second active agent or active ingredient. Examples of immunomodulatory compounds of the invention are disclosed herein (see, e.g., section 4.1); and examples of the second active agents are also disclosed herein (see, e.g., section 4.2).

In particular embodiments, one or more immunomodulatory compounds are administered in combination with the administration of one or more therapies that are used to treat, manage, or prevent myeloproliferative diseases. A non-limiting example is the use of immunomodulatory compounds of the invention in combination with the administration of an anti-cancer cocktail regimen, such as, but not limited to, a regimen that includes cytarabine and an anthracycline (e.g., daunorubicin or idarubicin).

Administration of the immunomodulatory compounds and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for an immunomodulatory compound is oral. Preferred routes of administration for the second active agents or ingredients of the invention are known to those of ordinary skill in the art. See, e.g., *Physicians' Desk Reference,* 1755-1760 (56$^{th}$ ed., 2002).

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of MPD being treated or managed, the severity and stage of MPD, and the amount(s) of immunomodulatory compounds of the invention and any optional additional active agents concurrently administered to the patient. In a particular embodiment, the second active agent is interferon-α, hydroxyurea, anagrelide, arsenic troxide, ST1571, imatinib mesylate, DX-8951 f, R115777, vincristine, daunorubicin, prednisone or a combination thereof. Interferon-α is administered in an amount of from 2 to 5 million unites subcutaneously three times weekly. Hydroxyurea is administered in an amount of from about 500 to about 1500 mg/d orally, adjusted to keep platelets <500,000/μL without reducing the neutrophil count to <2000/μL.

4.3.2 Use with Transplantation Therapy

In still another embodiment, this invention encompasses a method of treating, preventing and/or managing MPD, which comprises administering the immunomodulatory compound of the invention, or a pharmaceutically acceptable salt, solvate, hydrate, stereoisomer, clathrate, or prodrug thereof, in conjunction with transplantation therapy. As discussed elsewhere herein, the treatment of MPD is based on the stages and mechanism of the disease. As inevitable leukemic transformation develops in certain stages of MPD, transplantation of peripheral blood stem cells, hematopoietic stem cell preparation or bone marrow may be necessary. The combined use of the immunomodulatory compound of the invention and transplantation therapy provides a unique and unexpected synergism. In particular, an immunomodulatory compound of the invention exhibits immunomodulatory activity that may provide additive or synergistic effects when given concurrently with transplantation therapy in patients with MPD. An immunomodulatory compound of the invention can work in combination with transplantation therapy reducing complications associated with the invasive procedure of transplantation and risk of related Graft Versus Host Disease (GVHD). This invention encompasses a method of treating, preventing and/or managing MPD which comprises administering to a patient (e.g., a human) an immunomodulatory compound of the invention, or a pharmaceutically acceptable salt, solvate, hydrate, stereoisomer, clathrate, or prodrug thereof, before, during, or after the transplantation of umbilical cord blood, placental blood, peripheral blood stem cell, hematopoietic stem cell preparation or bone marrow. Examples of stem cells suitable for use in the methods of the invention are disclosed in U.S. provisional patent application No. 60/372,348, filed Apr. 12, 2002 by R. Hariri et al., the entirety of which is incorporated herein by reference.

4.3.3 Cycling Therapy

In certain embodiments, the prophylactic or therapeutic agents of the invention are cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one specific embodiment of the invention, an immunomodulatory compound of the invention is administered daily in a single or divided doses in a four to six week cycle with a rest period of about a week or two weeks. The invention further allows the frequency, number, and length of dosing cycles to be increased. Thus, another specific embodiment of the invention encompasses the administration of an immunomodulatory compound of the invention for more cycles than are typical when it is administered alone. In yet another specific embodiment of the invention, an immunomodulatory compound of the invention is administered for a greater number of cycles that would typically cause dose-limiting toxicity in a patient to whom a second active ingredient is not also being administered.

In one embodiment, an immunomodulatory compound of the invention is administered daily and continuously for 3 or 4 weeks at a dose of from about 0.1 to about 150 mg/d followed by a break of 1 or 2 weeks. Actimid™ is preferably administered daily and continuously at an initial dose of 0.1 to 5 mg/d with dose escalation (every week) by 1 to 10 mg/d to a maximum dose of 50 mg/d for as long as therapy is tolerated. In a particular embodiment, Revimid™ is administered in an amount of about 5, 10, or 25 mg/day, preferably in an amount of about 10 mg/day for three to four weeks, followed by one week or two weeks of rest in a four or six week cycle.

In one embodiment of the invention, an immunomodulatory compound of the invention and a second active ingredient are administered orally, with administration of an immunomodulatory compound of the invention occurring 30 to 60 minutes prior to a second active ingredient, during a cycle of 4 to 6 weeks. In another embodiment of the invention, the combination of an immunomodulatory compound of the invention and a second active ingredient is administered by intravenous infusion over about 90 minutes every cycle. In a specific embodiment, one cycle comprises the administration of from about 10 to about 25 mg/day of Revimid™ and from about 50 to about 200 mg/m²/day of a second active ingredient daily for 3 to 4 weeks and then one or two weeks of rest. In another specific embodiment, each cycle comprises the administration of from about 5 to about 10 mg/day of Actimid™ and from about 50 to about 200 mg/m²/day of a second active ingredient for 3 to 4 weeks followed by one or two weeks of rest. Typically, the number of cycles during which the combinatorial treatment is administered to a patient will be from about 1 to about 24 cycles, more typically from about 2 to about 16 cycles, and even more typically from about 4 to about 8 cycles.

4.4 Pharmaceutical Compositions and Single Unit Dosage Forms

Pharmaceutical compositions can be used in the preparation of individual, single unit dosage forms. Pharmaceutical compositions and dosage forms of the invention comprise an immunomodulatory compound of the invention, or a pharmaceutically acceptable salt, solvate, hydrate, stereoisomer, clathrate, or prodrug thereof. Pharmaceutical compositions and dosage forms of the invention can further comprise one or more excipients.

Pharmaceutical compositions and dosage forms of the invention can also comprise one or more additional active ingredients. Consequently, pharmaceutical compositions and dosage forms of the invention comprise the active ingredients disclosed herein (e.g., an immunomodulatory compound of the invention, or a pharmaceutically acceptable salt, solvate, hydrate, stereoisomer, clathrate, or prodrug thereof, and a second active ingredient). Examples of optional additional active ingredients are disclosed herein (see, e.g. section 5.2).

Single unit dosage forms of the invention are suitable for oral, mucosal (e.g., nasal, sublingual, vaginal, buccal, or rectal), or parenteral (e.g., subcutaneous, intravenous, bolus injection, intramuscular, or intraarterial), transdermal or transcutaneous administration to a patent. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the invention will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed by this invention will vary from one another will be readily apparent to those skilled in the art. See, e.g., *Remington's Pharmaceutical Sciences*, 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, this invention encompasses pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient.

Lactose-free compositions of the invention can comprise excipients that are well known in the art and are listed, for example, in the *US. Pharmacopeia (USP)* 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise an immunomodulatory compound of the invention, or a pharmaceutically acceptable salt, solvate, hydrate, stereoisomer, clathrate, or prodrug thereof in an amount of from about 0.10 to about 150 mg. Typical dosage forms comprise an immunomodulatory compound of the invention, or a pharmaceutically acceptable salt, solvate, hydrate, stereoisomer, clathrate, or prodrug thereof in an amount of about 0.1, 1, 2, 5, 7.5, 10, 12.5, 15, 17.5, 20, 25, 50, 100, 150 or 200 mg. In a particular embodiment, a preferred dosage form comprises 4-(amino)-2-(2,6-dioxo(3-piperidyl))-isoindoline-1,3-dione (Actimid™) in an amount of about 1, 2, 5, 10, 25 or 50mg. In a specific embodiment, a preferred dosage form comprises 3-(4-amino-1-oxo-1,3-dihydro-isoindol-2-yl)-piperidine-2,6-dione (Revimid™) in an amount of about 5, 10, 25 or 50 mg. Typical dosage forms comprise the second active ingredient in an amount of 1 to about 1000 mg, from about 5 to about 500 mg, from about 10 to about 350 mg, or from about 50 to about 200 mg. Of course, the specific amount of the second active ingredient will depend on the specific agent used, the type of MPD being treated or managed, and the amount(s) of immunomodulatory compounds of the invention, and any optional additional active agents concurrently administered to the patient.

4.4.1 Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences*, 18th ed., Mack Publishing, Easton Pa. (1990).

Typical oral dosage forms of the invention are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, PA), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form of the invention comprises an immunomodulatory compound of the invention, anhydrous lactose, microcrystalline cellulose, polyvinylpyrrolidone, stearic acid, colloidal anhydrous silica, and gelatin.

4.4.2 Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.4.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms of the invention. For example, cyclodextrin and its derivatives can be used to increase the solubility of an immunomodulatory compound of the invention, and its derivatives. See, e.g., U.S. Pat. No. 5,134,127, which is incorporated herein by reference.

4.4.4 Topical and Mucosal Dosage Forms

Topical and mucosal dosage forms of the invention include, but are not limited to, sprays, aerosols, solutions, emulsions, suspensions, or other forms known to one of skill in the art. See, e.g., *Remington's Pharmaceutical Sciences*, $16^{th}$ and $18^{th}$ eds., Mack Publishing, Easton Pa. (1980 & 1990); and *Introduction to Pharmaceutical Dosage Forms*, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms if desired. Examples of such additional ingredients are well known in the art. See, e.g., *Remington's Pharmaceutical Sciences*, $16^{th}$ and $18^{th}$ eds., Mack Publishing, Easton Pa. (1980 & 1990).

The pH of a pharmaceutical composition or dosage form may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

4.4.5 Kits

Typically, active ingredients of the invention are preferably not administered to a patient at the same time or by the same route of administration. This invention therefore encompasses kits which, when used by the medical practitioner, can simplify the administration of appropriate amounts of active ingredients to a patient.

A typical kit of the invention comprises a dosage form of an immunomodulatory compound of the invention, or a pharmaceutically acceptable salt salt, solvate, hydrate, stereoisomer, prodrug, or clathrate thereof. Kits encompassed by this invention can further comprise additional active ingredients such as, but not limited to, interferon-α, hydroxyurea, anagrelide, arsenic troxide, ST1571, imatinib mesylate, DX-8951f, R115777, vincristine, daunorubicin, prednisone, or a pharmacologically active mutant or derivative thereof, or a combination thereof. Examples of the additional active ingredients include, but are not limited to, those disclosed herein (see, e.g., section 4.2).

Kits of the invention can further comprise devices that are used to administer the active ingredients. Examples of such devices include, but are not limited to, syringes, drip bags, patches, and inhalers.

Kits of the invention can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodiun Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

EXAMPLES

The following studies are intended to further illustrate the invention without limiting its scope.

5.1 Pharmacology and Toxicology Studies

A series of non-clinical pharmacology and toxicology studies have been performed to support the clinical evaluation of an immunomodulatory compound of the invention in human subjects. These studies were performed in accordance with internationally recognized guidelines for study design and in compliance with the requirements of Good Laboratory Practice (GLP), unless otherwise noted.

The pharmacological properties of 3-(4-amino-1-oxo-1,3-dihydro-isoindol-2-yl)-piperidine-2,6-dione, including activity comparisons with thalidomide, have been characterized in in vitro studies. Studies examined the effects of 3-(4-amino-1-oxo-1,3-dihydro-isoindol-2-yl)-piperidine-2,6-dione or thalidomide on the production of various cytokines. In all studies, 3-(4-amino-1-oxo-1,3-dihydro-isoindol-2-yl)-piperidine-2,6-dione was at least 50 times more potent than thalidomide. In addition, a safety pharmacology study of 3-(4-amino-1-oxo-1,3-dihydro-isoindol-2-yl)-piperidine-2,6-dione has been conducted in dogs and the effects of 3-(4-amino-1-oxo-1,3-dihydro-isoindol-2-yl)-piperidine-2,6-dione on ECG parameters were examined further as part of three repeat-dose toxicity studies in primates. The results of these studies are described below.

5.2 Modulation of Cytokine Production

Inhibition of TNF-α production following LPS-stimulation of human PBMC and human whole blood by 3-(4-amino-1-oxo-1,3-dihydro-isoindol-2-yl)-piperidine-2,6-dione or thalidomide was investigated in vitro (Muller et al., *Bioorg. Med. Chem. Lett.* 9:1625-1630, 1999). The $IC_{50}$'s of 3-(4-amino-1-oxo-1,3-dihydro-isoindol-2-yl)-piperidine-2,6-dione for inhibiting production of TNF-α following LPS-stimulation of PBMC and human whole blood were ~100 nM (25.9 ng/mL) and ~480 nM (103.6 ng/mL), respectively. Thalidomide, in contrast, had an $IC_{50}$ of ~194 μM (50.2 μg/mL) for inhibiting production of TNF-α following LPS-stimulation of PBMC.

5.3 Toxicology Studies

The effects of 3-(4-amino-1-oxo-1,3-dihydro-isoindol-2-yl)-piperidine-2,6-dione on cardiovascular and respiratory function were investigated in anesthetized dogs. Two groups of Beagle dogs (2/sex/group) were used. One group received three doses of vehicle only and the other received three ascending doses of 3-(4-amino-1-oxo-1,3-dihydro-isoindol-2-yl)-piperidine-2,6-dione (2, 10, and 20 mg/kg). In all cases, doses of 3-(4-amino-1-oxo-1,3-dihydro-isoindol-2-yl)-piperidine-2,6-dione or vehicle were successively administered via infusion through the jugular vein separated by intervals of at least 30 minutes.

No animals died in this study. The cardiovascular and respiratory changes induced by 3-(4-amino-1-oxo-1,3-dihydro-isoindol-2-yl)-piperidine-2,6-dione were minimal at all doses when compared to the vehicle control group. The only statistically significant difference between the vehicle and treatment groups was a small increase in arterial blood pressure (from 94 mmHg to 101 mmHg) following administration of the low dose of 3-(4-amino-1-oxo-1,3-dihydro-isoindol-2-yl)-piperidine-2,6-dione. This effect lasted approximately 15 minutes and was not seen at higher doses. Deviations in femoral blood flow, respiratory parameters, and Qtc interval were common to both the control and treated groups and were not considered treatment-related.

All patents cited herein are incorporated by reference in their entireties. Embodiments of the invention described herein are only a sampling of the scope of the invention. The Fill scope of the invention is better understood with reference to the attached claims.

What is claimed is:

1. A method of treating myelofibrosis with myeloid metaplasia, which comprises administering to a patient having myelofibrosis with myeloid metaplasia from about 0.1 to about 2.0 mg per day of 4-(amino)-2-(2,6-dioxo(3-piperidyl))-isoindoline-1,3-dione, or a pharmaceutically acceptable salt or stereoisomer thereof.

2. The method of claim 1, wherein the compound is a free base.

3. The method of claim 1, wherein the compound is a pharmaceutically acceptable salt.

4. The method of claim 1, wherein the compound is a pharmaceutically acceptable stereoisomer.

5. The method of claim 4, wherein the stereoisomer is an enantiomerically pure R isomer.

6. The method of claim 4, wherein the stereoisomer is an enantiomerically pure S isomer.

7. The method of claim 1, wherein the patient has bone marrow fibrosis.

8. The method of claim 1, wherein the myelofibrosis with myeloid metaplasia is primary.

9. The method of claim 1, wherein the myelofibrosis with myeloid metaplasia is secondary.

10. The method of claim 1, wherein the compound is administered before, during or after transplanting umbilical cord blood, placental blood, peripheral blood stem cells, a hematopoietic stem cell preparation or bone marrow into the patient.

11. The method of claim 1, wherein the compound is administered orally.

12. The method of claim 1, wherein the compound is administered in the form of a capsule.

13. The method of claim 1, wherein the compound is administered in the form of a tablet.

14. The method of claim 1, wherein the compound is administered cyclically.

15. The method of claim 14, wherein one cycle comprises four to six weeks with a rest period of a week or two weeks.

16. A method of treating myelofibrosis with myeloid metaplasia, which comprises administering to a patient having myelofibrosis with myeloid metaplasia about 0.1 mg per day of 4-(amino)-2-(2,6-dioxo(3-piperidyl))-isoindoline-1,3-dione.

17. The method of claim 16, wherein the myelofibrosis with myeloid metaplasia is primary.

18. The method of claim 16, wherein the myelofibrosis with myeloid metaplasia is secondary.

19. The method of claim 16, wherein the patient is refractory to a conventional myeloproliferative disease treatment.

20. The method of claim 16, wherein the patient has bone marrow fibrosis.

21. The method of claim 16, wherein the compound is administered orally.

22. The method of claim 16, wherein the compound is administered in the form of a capsule.

23. The method of claim 16, wherein the compound is administered in the form of a tablet.

24. The method of claim 16, wherein the compound is administered cyclically.

25. The method of claim 24, wherein one cycle comprises four to six weeks with a rest period of a week or two weeks.

26. The method of claim 16, wherein the compound is administered before, during or after transplanting umbilical cord blood, placental blood, peripheral blood stem cells, a hematopoietic stem cell preparation or bone marrow into the patient.

\* \* \* \* \*